US009164067B2

(12) United States Patent
Gorenstein et al.

(10) Patent No.: US 9,164,067 B2
(45) Date of Patent: Oct. 20, 2015

(54) SYSTEM AND METHOD FOR TRACKING CHEMICAL ENTITIES IN AN LC/MS SYSTEM

(75) Inventors: Marc V. Gorenstein, Needham, MA (US); Guo-Zhong Li, Westborough, MA (US)

(73) Assignee: Waters Technologies Corporation, Milford, MA (US)

( * ) Notice: Subject to any disclaimer, the term of this patent is extended or adjusted under 35 U.S.C. 154(b) by 1618 days.

(21) Appl. No.: 10/588,855

(22) PCT Filed: Feb. 11, 2005

(86) PCT No.: PCT/US2005/004176
§ 371 (c)(1),
(2), (4) Date: Mar. 19, 2008

(87) PCT Pub. No.: WO2005/079261
PCT Pub. Date: Sep. 1, 2005

(65) Prior Publication Data
US 2008/0208485 A1  Aug. 28, 2008

Related U.S. Application Data

(60) Provisional application No. 60/544,501, filed on Feb. 13, 2004.

(51) Int. Cl.
*G01N 30/86* (2006.01)
*H01J 49/00* (2006.01)
*G01N 30/72* (2006.01)

(52) U.S. Cl.
CPC ........ *G01N 30/8665* (2013.01); *H01J 49/0036* (2013.01); *G01N 30/7233* (2013.01); *G01N 30/8679* (2013.01); *G01N 30/8693* (2013.01)

(58) Field of Classification Search
CPC . H01J 49/0036; G01N 30/86; G01N 30/8665; G06K 9/00
See application file for complete search history.

(56) References Cited

U.S. PATENT DOCUMENTS 4,740,903 A * 4/1988 Nakatsuka et al. ............. 702/32
5,602,755 A * 2/1997 Ashe et al. ..................... 702/30
(Continued)

FOREIGN PATENT DOCUMENTS

DE 103 24 149 A1 12/2004
JP 2002-181784 A 6/2002
(Continued)

OTHER PUBLICATIONS

Bylund, D., Danielsson, R., Malmquist, G. & Markides, K. Chromatographic alignment by warping and dynamic programming as a pre-processing tool for parafac modelling of liquid chromatography—mass spectrometry data. Journal of Chromatography A 961, 237-244 (2002).*
(Continued)

*Primary Examiner* — Soren Harward
(74) *Attorney, Agent, or Firm* — Muirhead and Saturnelli, LLC

(57) ABSTRACT

In complex separations, more than one entity may have the same molecular weight, to within the ability of an instrument to distinguish. Accurate mass measurements are used in light of the previously unknown regularities in retention time to determine a retention time (N pairs of values ($t_i^B$, $t_i^{B_{ref}}$)) (506). The retention time map allows a reference retention time to be assigned to each entity in a separation. The reference retention times, together with accurate mass measurements, can then be used to track and to compare entities (704,708) between separations.

14 Claims, 12 Drawing Sheets

(56) References Cited

U.S. PATENT DOCUMENTS

| | | | |
|---|---|---|---|
| 5,668,373 A * | 9/1997 | Robbat et al. | 250/339.12 |
| 5,885,841 A | 3/1999 | Higgs et al. | |
| 5,969,228 A * | 10/1999 | Gorenstein | 73/23.22 |
| 6,312,575 B1 | 11/2001 | Gorenstein | |
| 6,329,652 B1 * | 12/2001 | Windig et al. | 250/282 |
| 6,369,382 B1 * | 4/2002 | Ito et al. | 250/281 |
| 6,625,546 B2 | 9/2003 | Sepetov et al. | |
| 6,677,583 B2 | 1/2004 | Umemura | |
| 6,989,100 B2 | 1/2006 | Norton | |
| 2002/0023078 A1 * | 2/2002 | Liebler et al. | 707/1 |
| 2003/0040123 A1 * | 2/2003 | Hastings | 436/173 |
| 2004/0113062 A1 * | 6/2004 | Norton | 250/282 |
| 2004/0172200 A1 | 9/2004 | Kearney et al. | |
| 2005/0092910 A1 | 5/2005 | Geromanos et al. | 250/282 |
| 2005/0226536 A1 | 10/2005 | Fasulo | 382/294 |
| 2007/0095757 A1 | 5/2007 | Kaplan et al. | |
| 2010/0187414 A1 | 7/2010 | Gorenstein et al. | |

FOREIGN PATENT DOCUMENTS

| | | |
|---|---|---|
| JP | 2006-510875 A | 3/2006 |
| JP | 2006-528339 A | 12/2006 |
| JP | 2007-527992 A | 10/2007 |
| WO | WO 97/39347 | 10/1997 |
| WO | WO 03/054549 A2 | 7/2003 |
| WO | WO 03/095978 A2 | 11/2003 |
| WO | WO 03/102543 A2 | 12/2003 |
| WO | WO 2004/097582 A2 | 11/2004 |

OTHER PUBLICATIONS

Nielsen, N., Carstensen, J. & Smedsgaard, J. Aligning of single and multiple wavelength chromatographic profiles for chemometric data analysis using correlation optimised warping. Journal of Chromatography A 805, 17-35 (1998).*
Sweeley, C. C., Young, N. D., Holland, J. F. & Gates, S. C. Rapid computerized identification of compounds in complex biological mixtures by gas chromatography—mass spectrometry. Journal of Chromatography 99, 507-517 (1974).*
Cleveland, W. S. & Devlin, S. J. Locally Weighted Regression: An Approach to Regression Analysis by Local Fitting. J. Am. Stat. Assoc. 83, 596 (1988).*
DeCoster, J. Notes on Applied Linear Regression. (2003).*
Felinger, A. "Signal enhancement". Chapter 7 of Data Analysis and Signal Processing in Chromatography, 143-181 (Elsevier, 1998).*
European Search Report Dated May 27, 2008.
International Search Report Dated May 19, 2006.
Japanese Office Action and English Translation dated Aug. 17, 2010.

* cited by examiner

SYSTEM AND METHOD FOR TRACKING CHEMICAL ENTITIES IN AN LC/MS SYSTEM

This application claims the benefit of U.S. Provisional Application No. 60/544,501, filed Feb. 13, 2004, which is herein incorporated by reference in its entirety.

A portion of the disclosure of this patent document contains material which is subject to copyright protection. The copyright owner has no objection to the facsimile reproduction by anyone of the patent document or patent disclosure, as it appears in the Patent and Trademark Office patent file or records, but otherwise reserves all copyright rights whatsoever.

BACKGROUND

1. Field of the Invention

The present invention relates generally to LC/MS analysis systems. More particularly the present invention relates to tracking entities from one injection to another during LC/MS experiments

2. Background of the Invention

A key problem in analytical chemistry is the estimation of the concentration of one or more molecular entities contained within a complex mixture. Liquid chromatography (LC) followed by mass spectrometry (MS) is a well-known technique (LC/MS) that can be used to separate large numbers of chemical entities in a sample to facilitate measuring concentration or quantity of each chemical entity. Measuring the exact mass of an entity allows the entity to be tracked between samples. Measuring the response or intensity of the tracked entity allows the concentration of an entity to be tracked from sample to sample.

In LC/MS, a sample is injected into the system for analysis. For each such injection, the LC/MS system measures the retention time, molecular weight, and intensity of ions. Multiple ions may arise from a single molecule. The concentration of the molecule can be determined by examination by one or more of the ions it produces.

As used herein, the term "entity" can mean a single ion from a molecule or the set of ions obtained from a single, common molecule. For example a small molecule of low molecular weight can produce a single ion. A large molecule, such as a peptide or a protein, can produce multiple ions. Well-known techniques can be used to combine multiple ions from a molecule to obtain a single effective, mass, retention time, and intensity. It is assumed that each entity has a mass, retention time, and intensity, and that an effective mass, retention time, and intensity can be assigned to each entity.

Using these measurements of mass, retention time, and intensity, properties of the entities can be determined. For example, comparison of intensities of corresponding entities between injections is the basis of determining whether the concentration of an entity changes between control and unknown samples. Changes in a protein's concentration between samples are indicative of changes in expression level of the protein between samples.

A set of samples can be processed using sequential injections. The same sample can be injected multiple times to provide a set of replicate injections. For example, each of two distinct samples (a standard and an unknown) can be injected three times, thereby producing a total of six injections. Using this data, reproducibility of the concentration measurements can be inferred for each entity, as well as the change in concentration of each entity between the control sample and the unknown sample. Each sample may contain an amount of an internal standard to provide a relative calibration between samples.

For a technique to determine the concentration of any entity, it must first adequately resolve that entity from all others. The LC/MS technique allows for separation of entities (or the ions associated with an entity) in both mass and retention time. Entities that co-elute in retention time, which would otherwise be indistinguishable, can be resolved in mass, thus allowing for their detection and for an accurate estimate of their intensity.

However, for associating or tracking an entity from one injection to another, resolution by accurate mass alone may not be sufficient. For example, consider the properties of mass and retention time of a molecule. The molecular weight is an intrinsic property of a molecule. A mass spectrometer measures the ratio of the molecular weight to charge, m/z. The symbol $\mu$ is often used to indicate the mass-to-charge ratio, m/z. Values for $\mu$ can be compared directly between injections. Any variation in measured values of $\mu$ between injections for the same entity must be due only to instrumental noise sources.

Ionization techniques, such as electrospray ionization may allow determination of charge, Z, for samples such as peptides or proteins. The determined charge state allows inference of the molecular weight, m, of an entity. Consequently, molecular weight, m, provides a basis for tracking entities. For these purposes, the empirically observed mass-to-charge ratio value, $\mu$, or the inferred value of molecular weight, m, can be used, interchangeably. As used herein the term mass means the observed mass-to-charge ratio value, $\mu$ or the inferred molecular weight m.

With sufficiently high mass accuracy, each entity is potentially uniquely distinguishable based upon its value for mass. Thus, for a sample containing few entities, assuming sufficient chromatographic resolution to separate entities, a high accuracy mass spectrometer, such as a time-of-flight (TOF) analyzer with resolution of m/$\Delta$m$\approx$20,000, allows tracking of each entity from one injection to another based upon accurate measurements of mass alone. In such cases, mass is not necessarily being used to identify an entity in terms of its chemical composition or structure. Rather, mass is being used as an empirical and possibly unique identifier of the entity to track the entity between injections.

However, mass alone may not be sufficient to track an entity from one injection to another. If mass accuracy is low and the sample complex, then it is possible that the mass of an entity as seen in one injection may match the empirically observed mass of an unrelated entity in another injection. For example, there may be two entities where $\mu$ is 1024.200 amu and 1024.300 amu respectively. While such entities are distinguishable with MS accuracy less than 0.100 amu, they are not distinguishable using MS having accuracy greater than 0.100 amu.

The chromatographic retention time of an entity can be an additional, potentially independent identifier of that entity. An entity's retention time is not an intrinsic property. Rather, an entity's retention time depends on the interactions of the entity (or, rather the molecule that gives rise to the entity) with the liquid and solid phases in the chromatographic separation, among other effect. But, even though the retention time is not intrinsic, its value can be made highly reproducible for a given separation method. Ideally, if the retention time were exactly reproducible and to high accuracy, then the combination of agreement in both mass and retention time could well be sufficient to allow each entity to be uniquely tracked from one injection to another. That is, it would be highly unlikely that two different entities share the exact same mass and retention time. However, retention time is not exactly reproducible between injections. Rather, the retention time of an entity can wander from injection to injection.

Despite such retention time wander between injections, there is a known regularity in retention time. That is, if an entity elutes in injection A at time t, then that entity will elute in another injection, B, with a retention time that will lie within a window $t+\Delta t$. That is the retention-time of a given entity can wander from one injection to another. Such wander, however, is bounded by a window $t+\Delta t$. This bound $\Delta t$ can be determined empirically, and is termed herein the coarse retention time threshold, $\Delta t_c$. As used herein, the term $t+\Delta t_c$ refers to the coarse retention time window. Although it may be the case that all entities lying within a coarse retention window have sufficiently unique masses that tracking can be done on the basis of the coarse retention time window and mass alone, in general, and especially in the case of more complex samples, there are likely entities whose mass values do not render them unique within a given coarse retention time window.

BRIEF SUMMARY OF THE INVENTION

Embodiments of the present invention involve, but are not limited to, samples that are separate by LC, ionized with electrospray ionization, and analyzed by mass spectrometers, including quadrupoles, time of flight, ion traps, or combinations of these analyzers. In addition, the embodiments of the present invention are applicable to entities that can be fragmented by MS-MS or MS$^n$ techniques.

Embodiments of the present invention use additional heretofore unknown regularities in chromatographic retention time along with knowledge of entities having unique masses in a sample to uniquely track those remaining entities that might not otherwise be distinguishable by mass alone. Examples of such samples include digests of peptides that derive from natural protein samples. Peptide digests of blood serum, for example, can contain 10,000 or more distinct peptides, or entities. In a chromatographic separation, 30 or more peptides can elute within the width of a chromatographic peak.

A first heretofore unknown regularity is that if two different chemical entities elute at exactly the same retention time in one separation, then the difference in retention times for those entities in another separation will also be zero. That is, if two different chemical entities elute at the same time in one separation with respect to one another, they elute at the same identical retention time in all other separations with respect to one another. The absolute retention time of the pair may change from separation to separation. However, if the difference in retention time is zero for a pair of entities in one separation, the difference in retention time between that pair of entities will be zero for all separations.

This regularity occurs in the important case of peptide mixtures. Two peptides that elute at the same retention time in one separation will elute at identical retention time in all other separations. Again, while the absolute retention time may change from separation to separation, the retention time difference will be zero.

A second heretofore unknown regularity is the intrinsic measurement error associated with retention time. If two entities elute at the same retention time, relative to each other, in all injections, they will in fact elute at somewhat different measured elution times. Thus, within a single injection, the measured retention times of the two entities will match and be identical only on average. These measurement errors can be viewed as statistical errors associated with locating the top of peaks. For example, if an entity elutes at 10.0 minutes in an injection, its measured retention time might be expected to vary by ±0.2 minutes. if a second entity also elutes at 10.0 minutes, its measured retention time will also vary by +0.2 minutes. Thus, within an injection, the measured values of retention time for the two entities may be 9.90 and 10.15 minutes. This variation of 0.25 minutes is not a variation in the actual relative retention time of the two entities (which is zero). It is a variation in the measurement of retention times of each entity within that injection due to measurement error.

Generally, this statistical-based measurement error is significantly less that the wander error, described by $\Delta t_c$. The threshold associated with the intrinsic statistical measurement error is termed herein the fine retention time threshold, and denoted by $\Delta t_f$.

A third heretofore unknown regularity occurs for entities that elute closely in time, but not exactly at the same retention time. The retention-time at which such entities elute may change from separation to separation. However, if there is a third entity that elutes between the two close-in-time eluting entities, it will always elute between those two.

For example, as a result of retention time wander, the time offset between two entities may change from injection to injection. For example, if the entities elute at 2.0 and 2.4 minutes in one injection, they may elute at 2.5 and 2.7 minutes in a second injection. While it is true that the first entity's retention time drifted by 0.5 minutes between the injections, the amount of this drift is less important than the difference in retention times between the two entities. That difference was 0.4 minutes in the first injection and 0.2 minutes in the second injection.

The third heretofore unknown regularity also applies to a third entity that elutes in injection 1 between these two times. For example, assume that such a third entity elutes at 2.1 minutes in injection 1. According to the third regularity, since the third entity eluted between entities 1 and 2 in injection 1, it will also elute between entities 1 and 2 in other injections, such as injection 2. In addition, the offset between injections for the third entity is proportional. Thus, in injection 2, the third entity will elute at 2.55 minutes.

The regularity regarding the coarse time window (previously known) and the regularity concerning statistical errors or fine retention time threshold (previously unknown) occur in all chromatographic separations as they are characteristics of a reproducible measurement or a robust method. The regularity regarding relative retention times (previously unknown) and retention time order (previously unknown) may or may not occur for all entities in a complex mixture. However, they are observed in peptide digests, and likely hold for mixtures where the entities have related chemical interactions with the chromatographic stationary and moving phases.

Embodiments of the present invention can recognize the occurrence of these regularities and take advantage of them for the purpose of tracking entities from injection to injection. In an embodiment of the present invention, each entity in a sample is assigned a reference retention time. The reference retention time is unique in the sense that if two entities do not have the same reference retention time, they cannot be the same entity. If, on the other hand, they do have the same reference retention time, they can be the same entity.

Using this assumption, embodiments of the present invention track entities by requiring that they have the same mass and the same reference retention time. Entities that differ significantly in either or both molecular weight or retention time are not the same. According to embodiments of the present invention, a significant difference is one that falls outside a threshold.

In summary, in complex separations, more than one entity may have the same mass, to within the ability of instrument to distinguish. Embodiments of the present invention make use of accurate mass measurement in light of the aforementioned previously unknown regularities in retention time to determine a retention time map. The retention time map then allows a reference retention time to be assigned to each entity in a separation. The reference retention time and mass of an entity can then be compared between separations (injections) in order to track that entity from separation to separation (injection to injection).

In one embodiment, the present invention is a method for tracking entities in an LC/MS system. The method comprises choosing a subset of entities from a first injection and a subset of entities from a second injection. The entities chosen from the first and second injections are compared. Matching entities are identified based on the comparison. Using the matching entities a retention time map is constructed. The retention time map is used to assign a reference retention time to each entity. The reference retention time and mass of an entity can then be compared between separations (injections) in order to track that entity from separation to separation (injection to injection).

In another embodiment, the present invention is a system for tracking entities in an LC/MS system. The system comprises a sample that is input to a liquid chromatograph. The liquid chromatograph separates the sample into one or more entities. The system further includes a mass spectrometer into which the entities are input to determine a mass of each of the entities. A computer is included in the system. The computer is programmed for choosing a subset of entities from a first injection and a subset of entities from a second injection, comparing the entities chosen from the first and second injections, identifying matching entities in the first and second injections, constructing a retention time map based on the matching entities, assigning a reference retention time to each entity based on the map, and tracking an entity between separations (injections) using the reference retention time and mass of the entity.

DETAILED DESCRIPTION OF THE INVENTION

Figure 1:
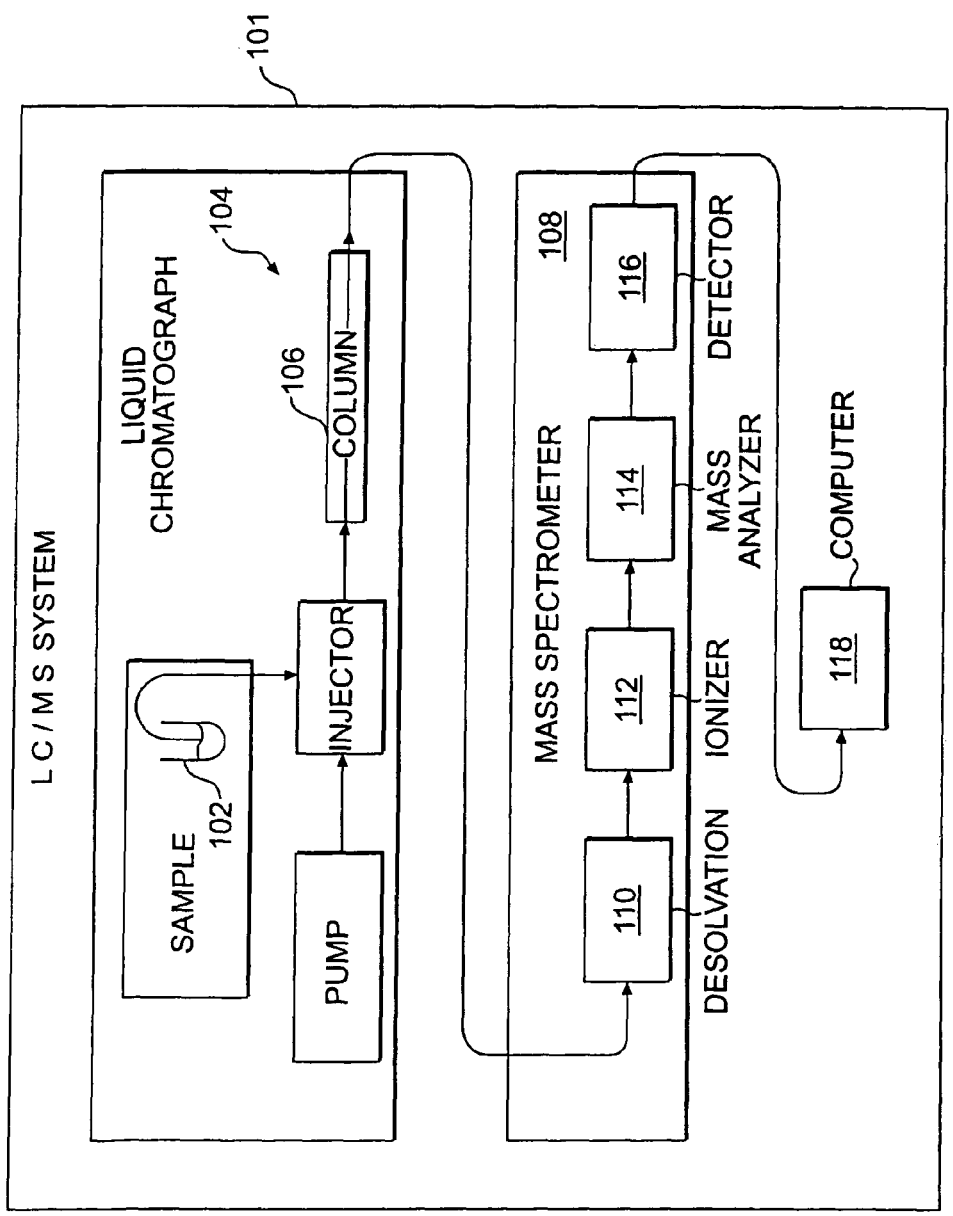
FIG. 1 is a schematic diagram of an LC/MS system according to an embodiment of the present invention.

FIG. 1 is a schematic diagram of an exemplary LC/MS system 101 according to an embodiment of the present invention. A sample 102 is automatically or manually injected into a liquid chromatograph 104. A high pressure stream of chromatographic solvent forces sample 102 to migrate through a chromatographic column 106 in liquid chromatograph 104. Column 106 typically comprises a packed column of silica beads whose surface comprises bonded molecules. Competitive interactions between the molecular species in the sample, the solvent and the beads determine the migration velocity of each molecular species. A molecular species migrates through column 106 and emerges, or elutes, from column 106 at a characteristic time, referred to as the retention time.

In an LC/MS system, upon elution from column 106, molecules are conveyed to a detector, such as mass spectrometer 108. Mass spectrometer 108 comprises a desolvation system 110, an ionizer 112, a mass analyzer 114, a detector 116, and a computer. Computer 118 can be any computer that can be configured or programmed to perform the entity tracking operations described herein. Further computer 118 can be configured to allow user input or automatic determination of values chosen as described herein.

When the sample is introduced into mass spectrometer 108, a desolvation system 110 removes the solvent, and ionizing source 112 ionizes the analyte molecules. Ionization methods include well-known electron impact (EI), electrospray (ES), atmospheric chemical ionization (APCI), matrix-assisted laser desorption ionization (MALDI), and thermospray. Note that in APCI the sample is desolvated, and then ionized.

The ionized molecules are conveyed to mass analyzer 114. Mass analyzer 114 sorts or filters the molecules by their mass-to-charge ratio. Mass analyzers, such as mass analyzer 114, include quadrupole (Q), time-of-flight (TOF) and fourier transform (FT) mass analyzers. Further, mass analyzers can be placed in a variety of tandem configurations, including for example, quadrupole time-of-flight (Q-TOF), triple quadrupole (Q1-Q2-Q3), and other quadrupole, time-of-flight configurations such as Q1-Q2-TOF.

According to embodiments of the present invention, a reference retention time is assigned to each entity in each injection. According to embodiments of the present invention the reference retention times and masses of entities are used to track entities between injections.

Reference retention times are obtained by selecting one injection as a reference injection (injection A) and comparing entities in A to entities found in other injections in the sample set. For example, consider two injections, injection A and injection B. Entities in the reference injection A are compared to those in injection B. From the results obtained from this comparison, the method assigns reference retention times to entities in injection B. Given a third injection, injection C, the method compares entities in A to those in C to obtain reference retention times for C. This procedure is repeated to assign reference retention times to all other entities in all other sample sets.

The reference retention times assigned to entities in B and C can then be directly compared to each other and/or to the retention times in A. In effect, a method according to embodiment of the present invention removes the effect of retention time drift between injections A and B, and between injections A and C for each entity in injections B and C. Embodiments of the present invention can be extended to as many injections of as many samples as desired.

According to embodiments of the present invention, a subset of the entities in injections A and B is used to obtain a retention-time map that describes retention time drift between injections A and B. From this map, a reference retention time is determined for all entities in injection B. Similarly, according to embodiments of the present invention, a subset of the entities in injections A and C is used to obtain a retention-time map that describes retention time drift between injections A and C. From this map, a reference retention time is determined for all entities in injection C. Embodiments of the present invention can be extended to determine the retention time maps between the reference injection A and as many injections of as many samples as desired.

Figure 2:
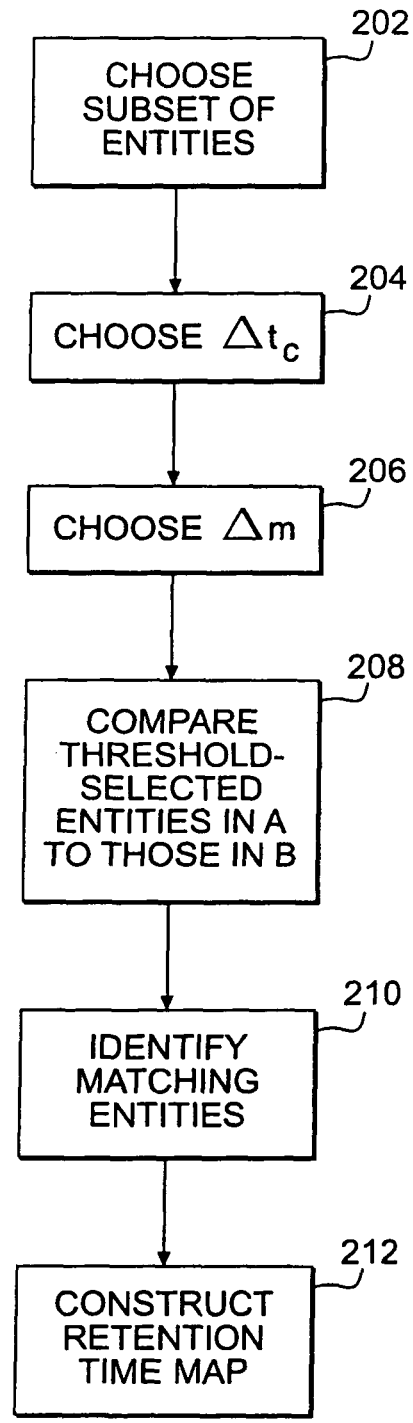
FIG. 2 is a flow chart for a method for identifying matching entities in order to determine a retention-time map between two injections A and B according to an embodiment of the present invention.

FIG. 2 is a flow chart for a method for identifying matching entities in order to determine a retention-time map between two injections A and B according to an embodiment of the present invention. The method can be performed automatically by a computer or in combination with inputs from a user.

In step 202, a subset of entities in injections A and B is chosen. The subset of entities can be chosen in a number of ways, and either manually or automatically. For example, the subset can be chosen based on intensity. In one such embodiment of the present invention, the subset of chosen entities includes those entities having an intensity higher than a threshold.

The threshold can be chosen in a number of ways. For example, the threshold could be a pre-determined threshold, entered manually, or determined in accordance with the collected data. One such threshold determined in accordance with the data is a median threshold. The median threshold is calculated as the median of all of the intensities measured for entities in an injection. Another threshold determined in accordance with the collected data is a threshold based on standard deviation of measured intensities in a particular injection. Although not required, the measured intensities in each injection could be normalized either before or after applying the threshold.

The subset of entities used in creating the retention time map includes those entities exceeding the threshold. Consequently, the subset of entities in the present example includes only those entities in injections A and B whose intensity exceeds the threshold.

In step 204 a coarse retention time threshold, $\Delta t_c$, is chosen. In an embodiment of the present invention, a preferred value for $\Delta t_c$ is 5 minutes. $\Delta t_c$ defines the maximum wander that can occur in retention time. The coarse retention time threshold can be chosen manually or automatically. In addition, the coarse retention time threshold can be pre-determined and stored, for example, in a configuration file from which it is read for step 204.

In step 206 a molecular weight threshold, $\Delta m$, is chosen. The molecular weight threshold is alternately referred to herein as a mass threshold. The molecular weight threshold can also be expressed as parts per million $(\Delta m/m)*10^6$ or as a mass-to-charge ratio, $\Delta u$. The molecular weight threshold can be obtained through knowledge of the properties of the MS using methods well-known to those skilled in the art. For example, one such method is to specify the molecular weight threshold in terms of the width of a spectral peak. If the spectral peak width is specified as the full-width-at-half maximum (FWHM), the threshold in ppm can be expressed as $(FWHM/m)*10^6$. For high intensity peaks, this threshold can be reduced by using a fraction of the FWHM, such as 0.2, thus the ppm error is $(0.2*FWHM/m)*10^6$.

The molecular weight threshold can be chosen manually or automatically. In addition, the molecular weight threshold can be pre-determined and stored, for example, in a configuration file from which it is read for step 206.

In step 208, a search is performed that compares all threshold-selected entities in injection A to those in injection B. Entities in injection A that singly match an entity in injection B are identified in step 210. Two entities are considered to match if the magnitude of the difference in their masses falls below the mass threshold $\Delta m$, if the magnitude of the difference in their retention times falls within the coarse retention time threshold $\Delta t_c$, if there is only a single entity in B that meets that criteria, and if the intensity of both entities (the entity in injection A, and the possible matching entity in injection B) lie above the respective median intensities. Search methods that can identify such matching entities in light of the above disclosure are well-known in the art.

The resulting set of pairs obtained in Step 210 contain only pairs of entities that possess the unique match characteristics of molecular weight, coarse retention time and that satisfy any intensity requirements. That is the set contains N matched-pairs of entities, each indicated by a subscript i, and each satisfying the following conditions:

$$|m_i^B - m_i^A| < \Delta m;$$

$$|t_i^B - t_i^A| < \Delta t_c;$$

$$I_i^A > \text{median}(I^A); \text{ and}$$

$$I_i^B > \text{median}(I^B).$$

It would be apparent to those skilled in the art that other requirements could be enforced that define singly matching entities. These other requirements could be in addition to, alternative to, or in combination with one or more of the foregoing requirements. For example, a requirement that intensity ratios fall within a particular threshold could be added. Under such a condition, matching entities must satisfy the condition:

$$\frac{I_i^A}{I_i^B} < r \text{ and } \frac{I_i^A}{I_i^B} > \frac{1}{r}.$$

In such a case a preferred value for r might be 2.

Another requirement that could be added applies if ions of known charge state are being compared. In such a case, a requirement that charge states match could be added, such that $Z_i^A = Z_i^B$.

Pairs of matching entities from injections A and B are then obtained by executing a search according to an embodiment of the present invention, as described in Steps 202 to 210. These pairs of entities are retained only if the entities in injections A and B meet the threshold criteria. That is, the effect of steps 202 to 210 is to pick a subset of entities in injections A and B that satisfy match criteria that consist of the mass threshold, coarse retention time threshold, and a possible intensity threshold.

From these pairs of retained, matched entities a delta retention time, defined as $\Delta t_i \equiv t_i^B - t_i^A$, is obtained for each pair. The delta retention time $\Delta t_i$ is the retention time drift of an entity in injection B relative to that entity in injection A at retention time $t_i^B$. The two retention times $t_i^A$ and $t_i^B$ are the ith retained matched pair from injection A and B.

Figure 3:
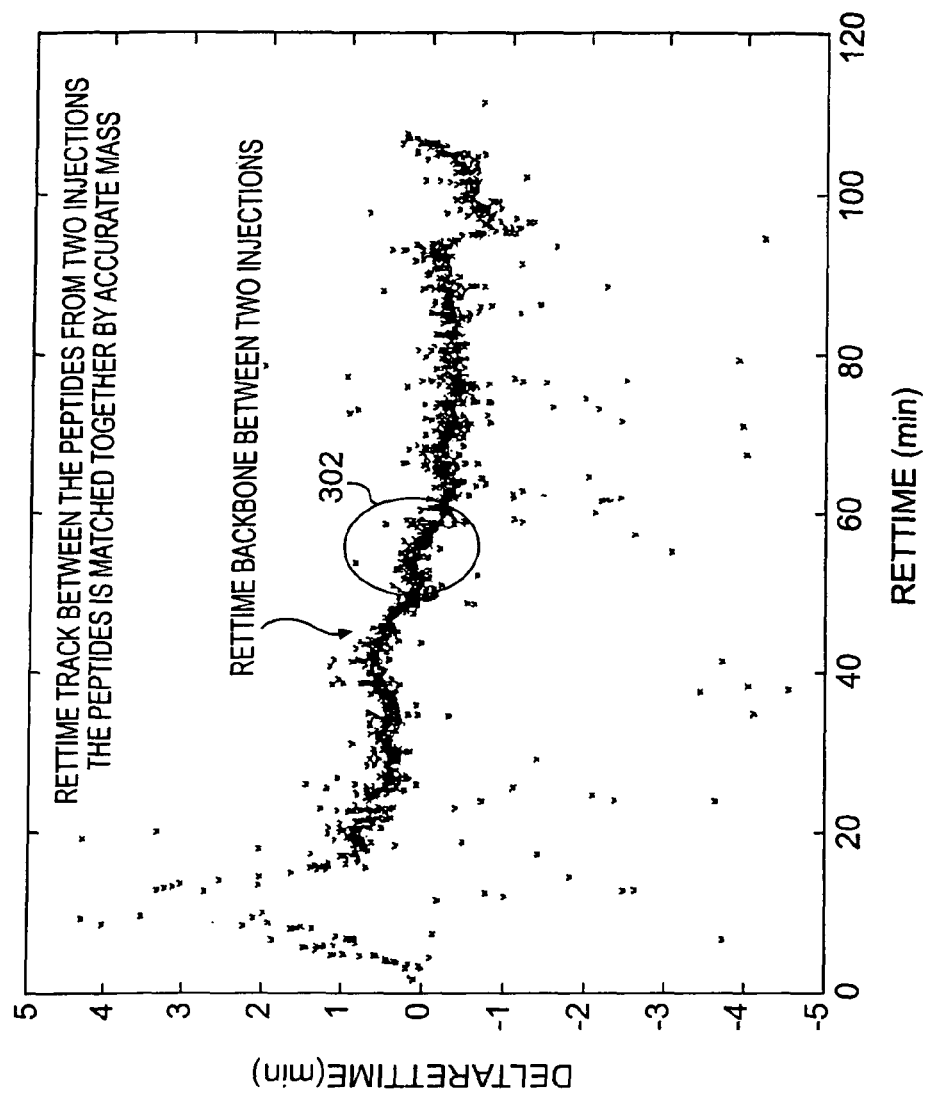
FIG. 3 is an exemplary plot of points retained executing a mass threshold and coarse retention-time threshold search according to an embodiment of the present invention.

FIG. 3 is an exemplary plot of $\Delta t_i$ versus $t_i^B$ obtained from pairs retained after identifying matching entities (Step 210). The points in FIG. 3 correspond to entities in injections A and B that meet the threshold criteria. In the example plot of FIG. 3, threshold criteria are that the entities must agree within a mass threshold, $\Delta m$, of 0.020 amu and have a retention time difference within 5 minutes, the coarse retention time threshold, and the median intensity threshold.

Figure 4:
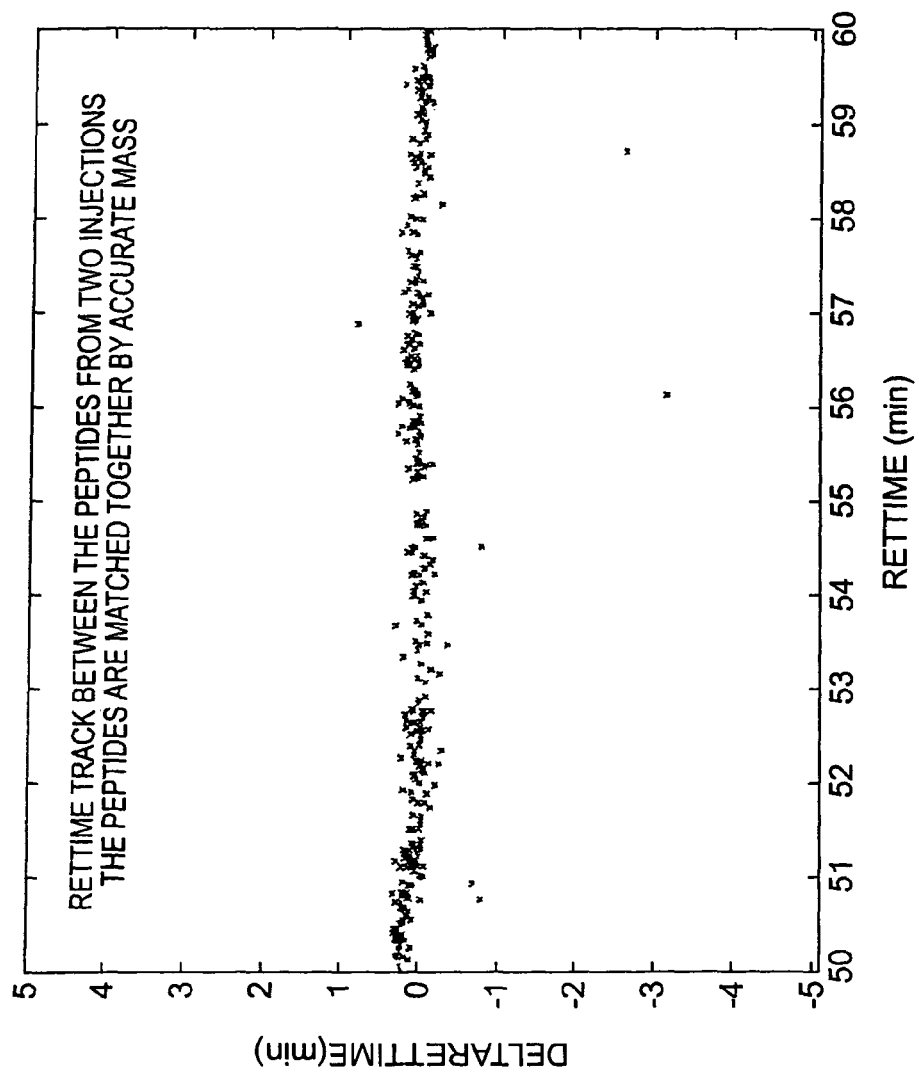
FIG. 4 is an exemplary plot of points retained after executing mass threshold and coarse retention-time threshold search with the horizontal axis expanded according to an embodiment of the present invention.

FIG. 4 is an exemplary plot of area 302 in FIG. 3 expanded according to an embodiment of the present invention. The expanded horizontal axis illustrates how concentrated the matched pairs are on the vertical axis.

Examination of FIGS. 3 and 4 reveals the presence of a dense backbone along which most of the points cluster. However, the figures also reveal some scattering of points about the backbone, and the presence of outliers. These issues can be addressed through techniques such as filtering described below.

Figure 5:
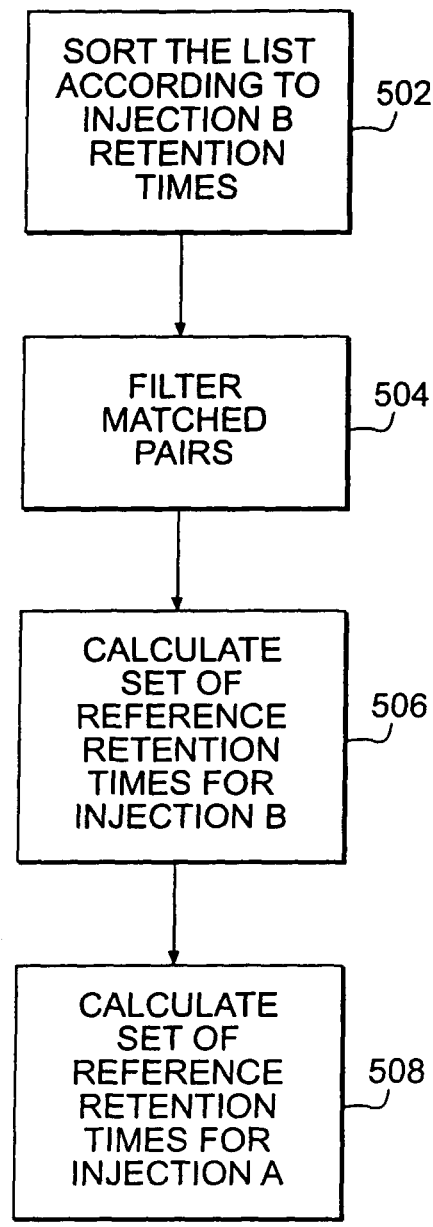
FIG. 5 is a flow chart for a method for using matching entities to construct a retention time map according to an embodiment of the present invention.

Once the list of matched entities is identified using the mass threshold and coarse retention time threshold, a retention time map is constructed in step 212. FIG. 5 is a flow chart for a method for constructing a retention time map according to an embodiment of the present invention. In step 502, the list of matched pairs is sorted according to the retention times observed during injection B. In a preferred embodiment, the list is sorted so that the values of $t_i^B$ are in ascending order. Thus, $t_{i+1}^B > t_i^B$ for i=1, 2, ..., N−1. The sorting preserves the pairing between entities in injections A and B that resulted from the mass and coarse retention time search.

Examination of the plot shown in FIG. 3 confirms the selection of the value for $\Delta t_c$ as most of retention time differences fall within the coarse retention time window. Moreover, such examination suggests that a reduced value of $\Delta t_c$ could have been used to determine the pairing between entities, i.e., the value of $\Delta t_c$ can be refined. If on the other hand, it appeared from examination of a plot such as that illustrated in FIG. 3 that the excursion exceeded the value of $\Delta t_c$, the value of $\Delta t_c$ could be increased, and the steps 204-210 for determining matching pairs illustrated in FIG. 2 could be repeated.

In step 504 the values of $\Delta t_i$ are filtered to find a refined value for $\Delta t_i$, as a function of $t_i^B$. Such filtering can be performed in a number of ways. For example, the filtering can be a moving average filter, a median filter, a spline, or any other desired filtering. With a moving average filter, each value of $\Delta t_i$ is replaced by a weighted average of its neighbors. However, to eliminate the effects of the outliers, a median average filter is employed for purposes of the present disclosure. In a median average filter, each value of $\Delta t_i$ is replaced by the median of itself and its M nearest neighbors. Typically, M ranges from 5 to 20, though it could be outside of that range for a particular application.

Figure 8:
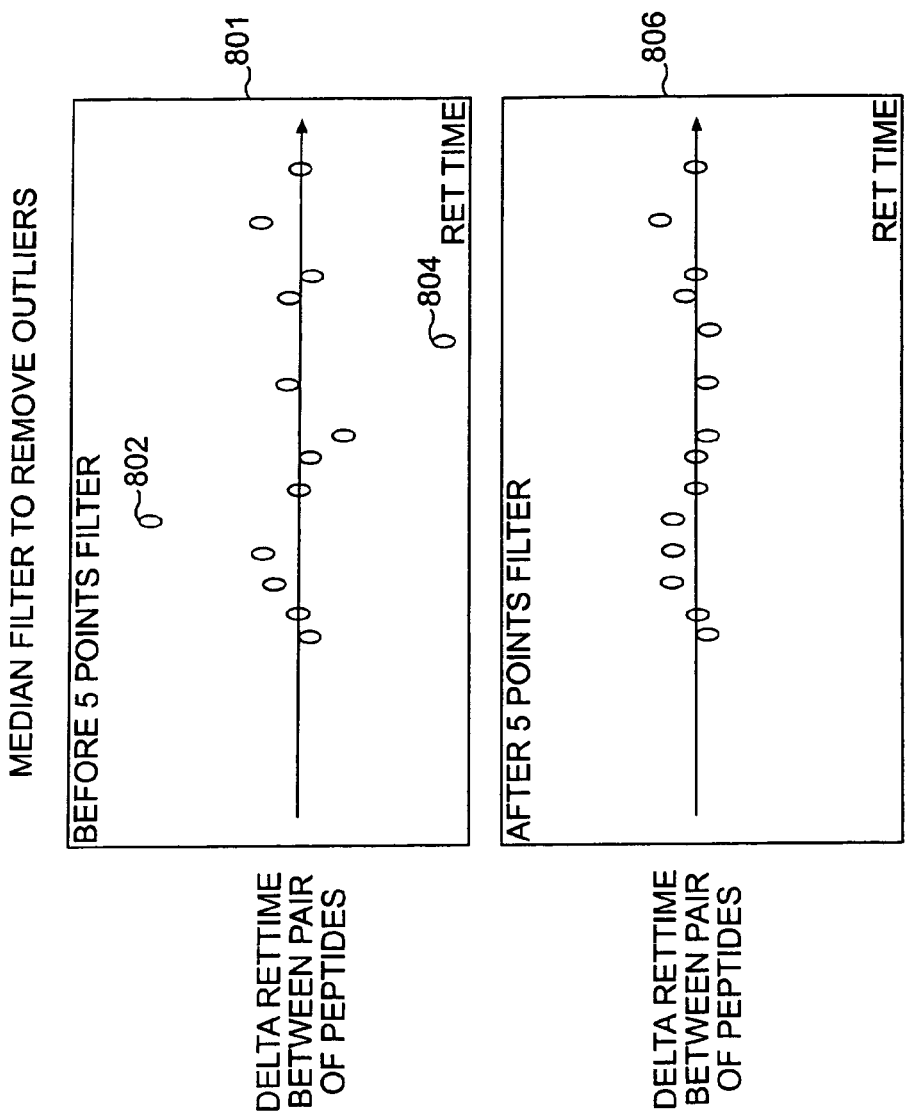
FIG. 8 illustrates application of a 5-point median filter to an exemplary data set.

FIG. 8 illustrates application of a 5-point median filter to an exemplary data set to remove outliers. Plot 801 plots the data set prior to application of the 5-point median filter. Two outliers, 802 and 804 are prominent in plot 804. Plot 806 illustrates the data set after application of the 5-point median filter. It can readily be seen that the 5-point median filter eliminated outliers 802 and 804.

Figure 9A:
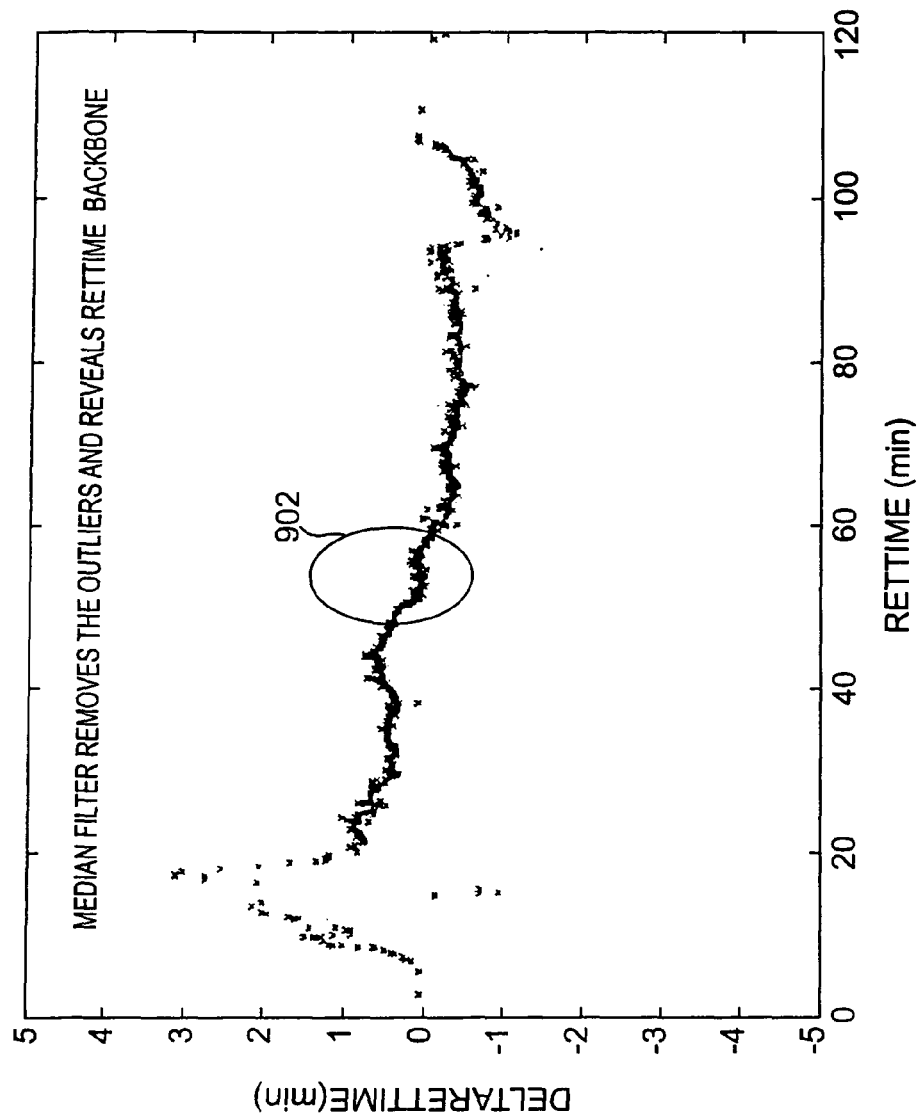
FIGS. 9a and 9b are plots of the results of applying a 5-point median filter to the data illustrated in FIGS. 3 and 4 respectively in order to determine the retention time map and the fine retention time threshold, according to an embodiment of the present invention.
Figure 9B:
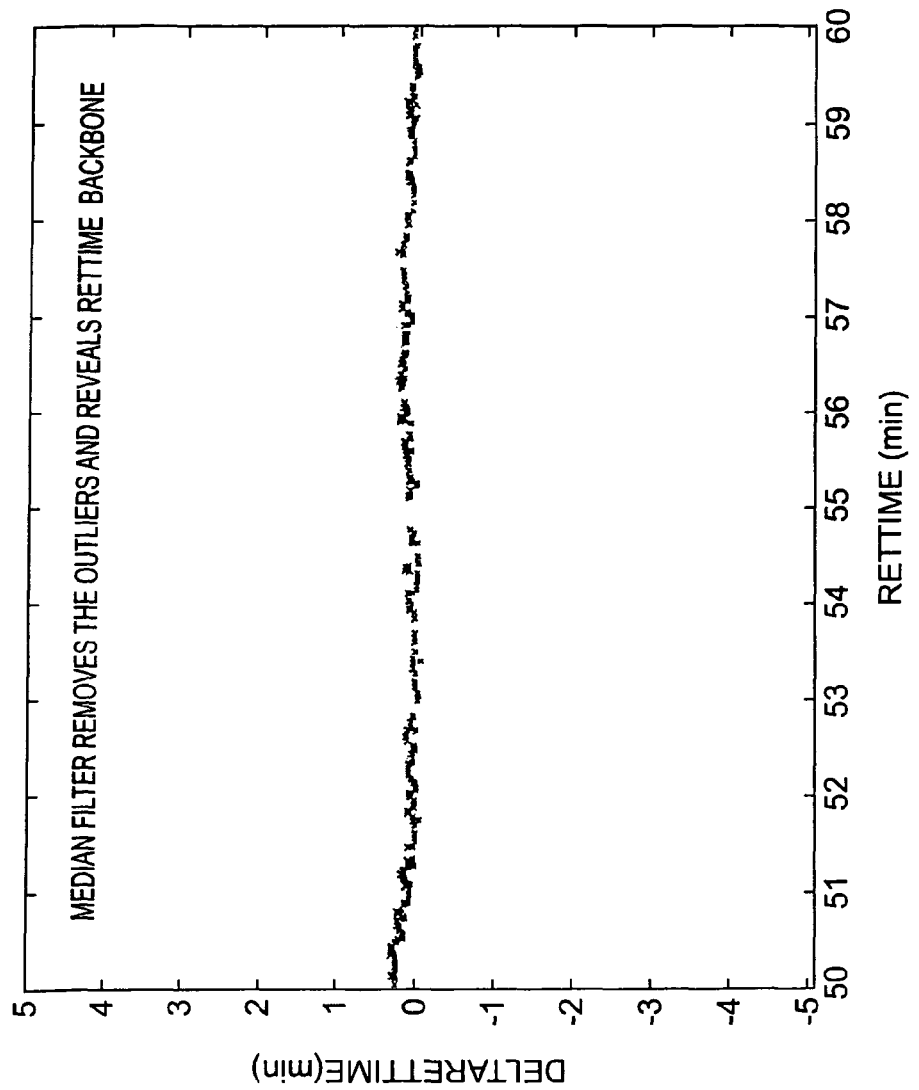

Filtering by the median filtered generates the set of median filtered values $\Delta t_i^m$, corresponding to retention times $t_i^B$. FIGS. 9a and 9b are plots of the result of applying a 5 point median filter to the exemplary data illustrated in FIGS. 3 and 4 respectively, according to an embodiment of the present invention. FIG. 9b is area 902 of FIG. 9a expanded. Examination of FIGS. 9a and 9b reveals the removal of outliers by the median filter. We refer to the set of points ($\Delta t_i^m$, $t_i^B$) plotted in FIGS. 9a and 9b as the backbone. The plot of $\Delta t_i^m$ versus $t_i^B$ in FIGS. 9a and 9b passes through the center of the densest regions in FIGS. 3 and 4.

In step 506, a set of reference retention times is calculated as $t_i^{Bref} \equiv t_i^B - \Delta t_i^m$. The effect of this equation is to subtract the filtered retention time drift $\Delta t_i^m$ from $\Delta t_i^B$. The value $t_i^{Bref}$ is the retention time that entity is would have if it were in injection A. Step 506 results in N pairs of values, ($t_i^B$, $t_i^{Bref}$). These pairs of values are the retention time map between the two injections.

The retention time map ($t_i^B$, $t_i^{Bref}$) can be viewed as a point-to-point look-up table (LUT), which is described by the paired values. As described above, the retention time map is derived from a subset of the entities. Using the retention time map, a reference retention time is determined for all entities in injection B. Specifically the retention time map is used to determine reference retention times for all entities in injection B whether they are or are not in the LUT.

Figure 6:
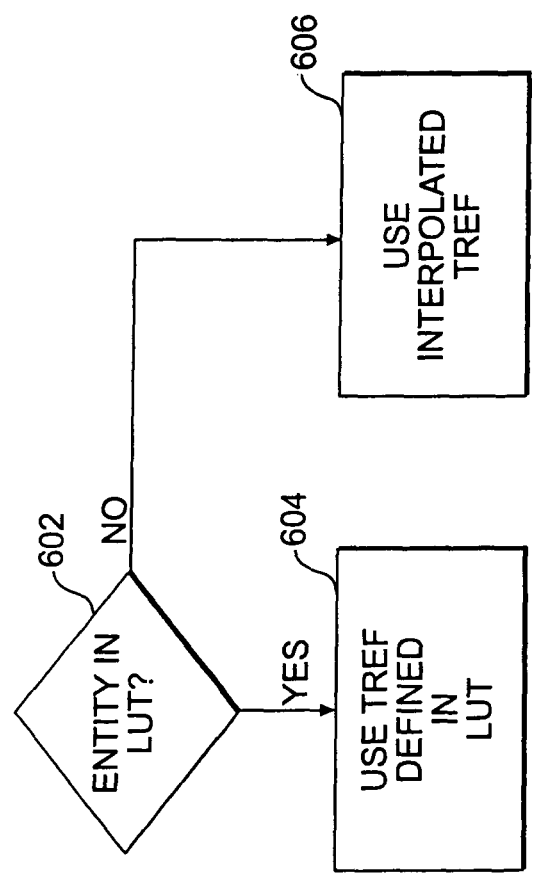
FIG. 6 is flow chart for a method for using the retention time map to determine reference retention times according to an embodiment of the present invention.

FIG. 6 is a flow chart for a method for using the retention time map to determine reference retention times for all entities in injection B according to an embodiment of the present invention. In step 602, it is determined if a given entity in injection B is part of the look-up table. Whether the entity is a part of the LUT is based on its retention time, $t_i^B$. If the entity's retention time is included in the LUT, the entity is considered to be included in the retention time map. Otherwise, the entity is not considered as included in the retention time map.

If an entity is included in the retention time map, then its reference retention time is $t_i^{Bref}$ as defined above in step 506. If, on the other hand, the entity in injection B is not part of the retention time map LUT, then in one embodiment of the present invention, linear interpolation is applied to calculate to the reference retention time for the entity in injection B. The equation for the linear interpolation is given as:

$$t_k^{Bref} = t_i^{Bref} + (t_k^B - t_i^B) \frac{t_{i+1}^{Bref} - t_i^{Bref}}{t_{i+1}^B - t_i^B}$$

where $t_{i+1}^B > t_k^B \geq t_i^B$. The entities specified by subscripts i and i+1 specify entities included in the retention time map, i.e., in the LUT. The entities specified by the subscript k are not included in the LUT. Thus, the interpolation equation specifies how reference retention times are determined for entities not included in the LUT.

In step 508 retention reference times are calculated for all entities in injection A. In a preferred embodiment of the present invention, the reference retention time for each entity in injection A is its original retention time. That is, for all entities in injection, the retention reference time $t_i^{Aref} \equiv t_i^A$. After the reference retention times for entities in injection A have been assigned, a reference retention time has been assigned for all entities in injections A and B. The foregoing assignment of reference retention times to each of the entities in injections A and B removes the retention time offset between entities in injections A and B.

Additional injections, if available, can also be considered. For example, if a third injection, injection C, were available, the above described steps could be repeated, substituting the values for entities in injection C in place of those of injection B to determine $t_i^{C_{ref}}$.

Thus embodiments of the present invention can determine reference retention times for all entities in all injections in a sample set. The reference injection (herein, injection A) can be taken to be any injection within such a sample set for the purpose of determining reference retention times for entities within a sample set.

Figure 7:
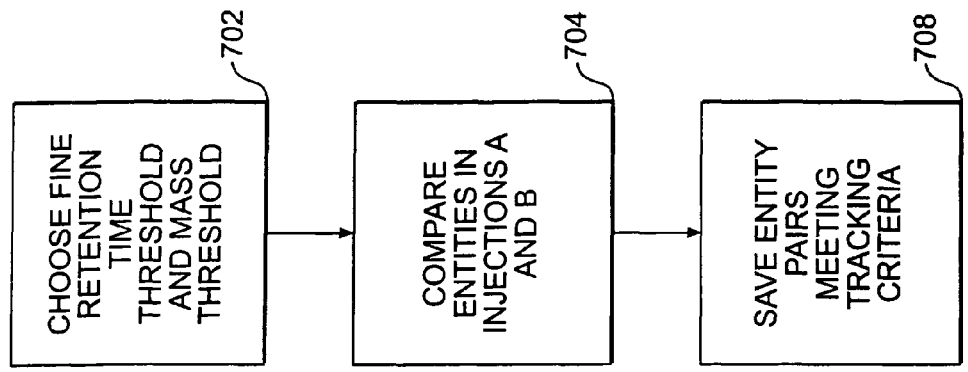
FIG. 7 is a flow chart for a method for using reference retention times and masses to track entities across injections according to an embodiment of the present invention.

FIG. 7 is a flow chart for a method for tracking the entities in injections A and B. Given the retention time map created according to an embodiment of the present invention, step 702 determines the fine retention time threshold, $\Delta t_f$. The fine retention time threshold is the intrinsic statistical error in measurements of a peak's retention time.

The fine retention time threshold $\Delta t_f$ is computed by considering the delta retention time values $\Delta t_i$ found for each matched pair and the filtered values $\Delta t_i^m$. Given $\Delta t_i$ and $\Delta t_i^m$, the differences of these values is computed as $\delta t_i^m \equiv \Delta t_i - \Delta t_i^m$. Some values of $\delta t_i^m$ are zero, when the median value for $\Delta t_i$ is $\Delta t_i$ itself. These zero values are omitted, creating a set of points $\delta t_i$. The values for $\delta t_i$ represent the intrinsic statistical error in the measurement of retention time.

$\Delta t_f$ can be estimated from $\delta t_i$ by, for example, taking the standard deviation about the mean of $\delta t_i$ and assigning $\Delta t_f$ to be 4 times that standard deviation. Alternatively $\Delta t_f$ can be estimated from $\delta t_i$ by using well-known histogramming techniques, where a histogram of $\delta t_i$ is produced and $\Delta t_f$ corresponds to a time that includes a specified fraction of the points, e.g. 99%. $\Delta t_f$.

In tracking entities between injections, the retention time threshold that will be used in the fine retention time threshold $\Delta t_f$. The fine retention time threshold is used in conjunction with the reference retention times, and mass values, to track entities between injections. Typically, $\Delta t_f$ is on the order of 0.4 minutes but may vary from application to application. Thus, the retention time threshold has been reduced from the coarse retention time threshold of 5 minutes to approximately 0.4 minutes. In turn, this reduction has the effect of reducing or eliminating ambiguities in comparing entities having the same molecular weight.

Using $\Delta t_f$, all entities in injections A, B and C can be tracked. In step 704, all entities in injections A and B are compared. Those meeting the tracking criteria are retained. For example, in a preferred embodiment of the invention, the tracking criteria are:

$$|m_i^A - m_j^B| < \Delta m \text{ and}$$

$$|t_i^{A_{ref}} - t_j^{B_{ref}}| < \Delta t_f.$$

The search is over any entity (indexed by i) in injection A versus any entity (indexed by j) in injection B. As can be seen by the tracking criteria provided above, the mass window (mass threshold) is unchanged, whereas the retention time window (retention time threshold) is changed to compare reference retention times, not the retention times themselves, to the fine search threshold. A match is indicated when both criteria are met. Though optional, application of intensity criteria is not required.

Additional injections can be analyzed. For example, given a third injection, injection C, all entities in injection C are compared to all entities in injection A. Only those entity pairs meeting the following criteria are retained:

$$|m_i^A - m_j^C| < \Delta m \text{ and}$$

$$|t_i^{A_{ref}} - t_j^{C_{ref}}| < \Delta t_f.$$

Alternatively, all entities in injection C could be compared to all entities in injection B. Only those entity pairs meeting the following criteria are retained:

$$|m_i^C - m_j^B| < \Delta m \text{ and}$$

$$|t_i^{C_{ref}} - t_j^{B_{ref}}| < \Delta t_f.$$

Note that even though injection A is used as the common target for the reference retention time computation, once computed, reference retention times can be compared between any two injections, such as between B and C. Thus, embodiments of the present invention provide a completely symmetric comparison for entity tracking across an arbitrarily large number of injections.

Figure 10A:
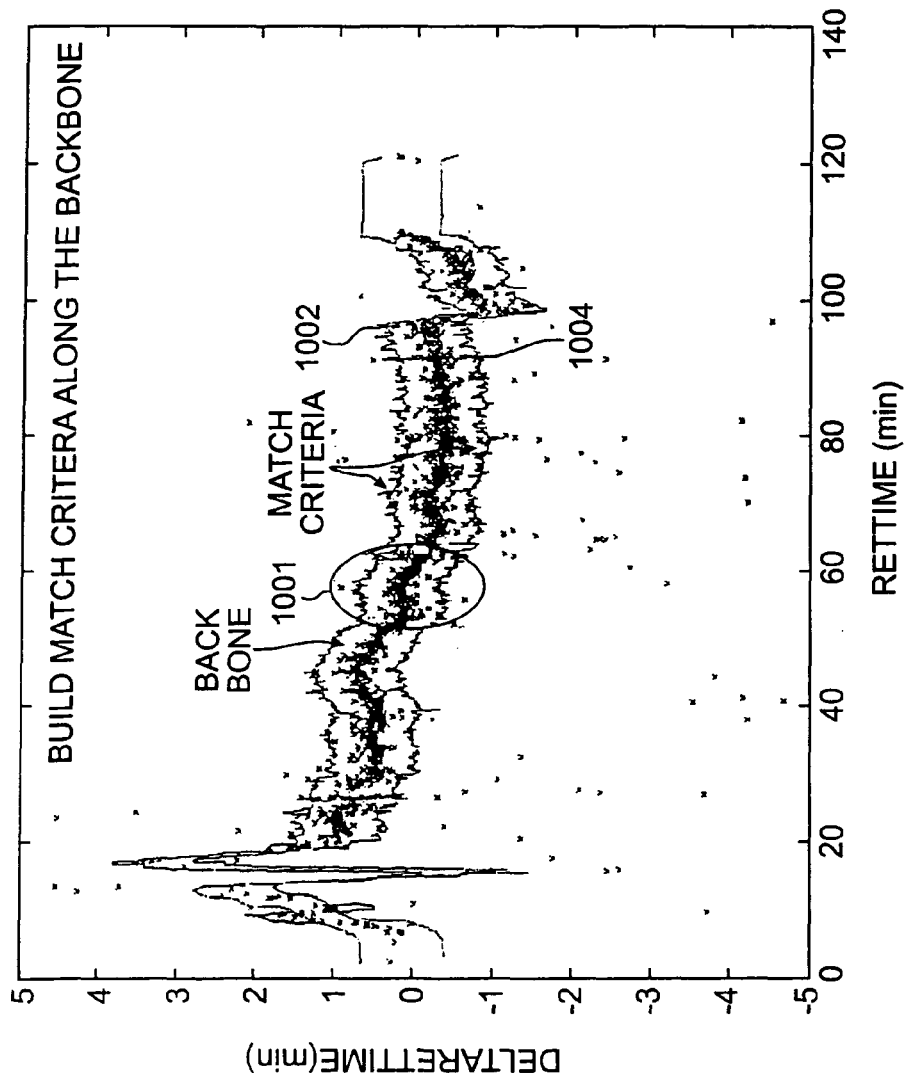
FIGS. 10a and 10b are plots illustrating use of the reference retention time, fine retention time threshold, mass, and mass threshold to track entities between injections, according to an embodiment of the present invention.
Figure 10B:
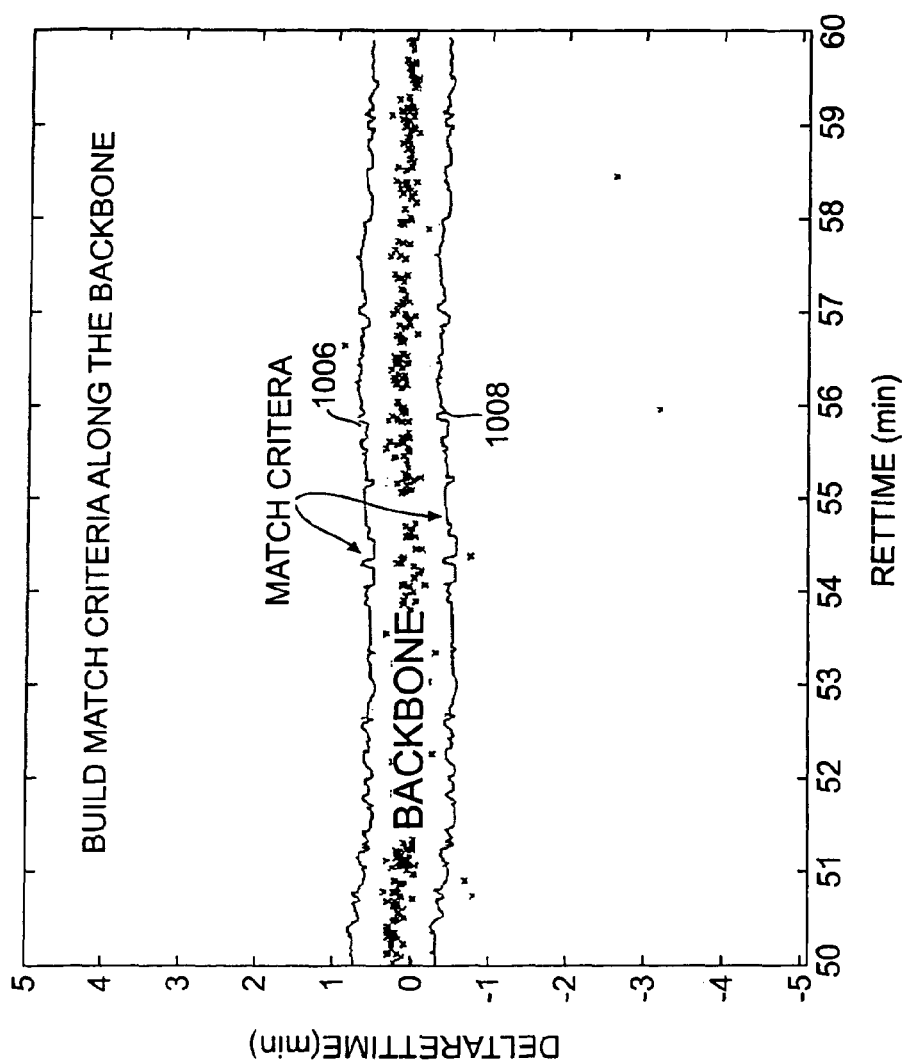

FIGS. 10a and 10b are plots illustrating use of the fine retention time threshold for tracking entities between injections according to an embodiment of the present invention. Lines 1002 in FIG. 10a is obtained by adding the fine retention time threshold to the backbone $\Delta t_f + \Delta t_i^m$, and line 1004 is obtained by subtracting the fine retention time threshold from the backbone $\Delta t_f - \Delta t_i^m$. FIG. 10b is a plot of area 1001 of FIG. 10a expanded. Lines 1006 and 1008 are expanded view of lines 1002 and 1004.

In FIG. 10a, those points that lie within 1002 and 1004 satisfy $|t_i^{A_{ref}} - t_j^{B_{ref}}| < \Delta t_f$. Therefore each point that lies within 1002 and 1004 represents a pair of entities tracked between injection A and B. This is because each point simultaneously satisfies two criteria: the fine retention time threshold $|t_i^{A_{ref}} - t_j^{B_{ref}}| < \Delta t_f$ and the mass threshold $|m_i^A - m_j^B| < \Delta m$.

In summary, embodiments of the present invention allow tracking of entities between injections. For example, in an embodiment of the present invention two entities are the same if they have the same molecular weight (within a prior specified error) and if they have the same reference retention time (to within a prior specified error). The errors can be determined by examining data properties. Such tracking of entities over injections allows an analyst to quantify or track relative changes in concentration of entities between samples in a sample set.

As can be seen, embodiments on the present invention do not require use internal standards as is required using conventional entity tracking methods. This is because embodiments of the present invention do not require a priori knowledge of which entities appear with unique masses. In effect, the exact mass measurements allow use of each entity appearing in the retention time map as a local retention time standard.

Assignment of reference retention times requires that there be a coarse and a fine retention time threshold. The coarse threshold provides boundary limits that are not to be exceeded. The fine threshold provides variation about zero. All unique matches for entities having high-intensity (e.g., high signal-to-noise ratio) are expected to be found within the coarse threshold.

Once an entity has been tracked from injection to injection, the quantitative change in concentration of the entity between samples can be measured. The quantitative response is the response as measured by the LC/MS system for the ion or set of ions that define an entity.

For example, consider an experiment that includes of N replicate injections for each of M samples. The mean, median, standard deviation, coefficient of variation can be obtained for mass, intensity and retention time for all entities tracked within each subset of N replicate injections. The mean of these quantities can be similarity tracked for each entity between the M samples.

The response of each entity as a function of sample can be input to standard statistical analysis software, such as SIMCA (available from Umetrics, Switzerland), or Pirouette (available from Infometrix, Woodenville, Wash., USA). Such analysis software can take as input the list of tracked entities produced by embodiments of the present invention and reveal changes in entities between sample populations. The SIMCA and Pirouette software packages, as well as other software systems, provide principle component analysis or factor analysis techniques that can be applied to these data.

In particular, intensities associated with tryptic peptides that are digestion fragments of a common protein change in concert from sample to sample. Consider the following: one sample or set of samples contains a protein that is expressed at one level, and another sample or set of samples contain the same protein but now is expressed at a different concentration level. If tryptic digestion is performed, then the concentration of the tryptic peptides associated with that protein will scale from one sample to another. That is, the concentration pattern will form one distinct pattern in one sample, and will from a similar patter in another sample, but with intensity values scaled overall to be larger or smaller, in response to a larger or smaller concentration of the parent protein.

Such correlated change in concentrations can be readily seen by factor analysis methods or by methods based on principle component analysis (PCA). Such a method can be used to identify the parent proteins whose concentration, or expression level, has changed from sample to sample. That is, if a set of peptides produce a distinctive signature in a PCA plot. If those peptides point to a common parent protein, then the protein whose expression level has changed has been identified.

A definitive identification can be made by taking the exact mass of these associated peptides (the ones that change in concert) and identifying them using standard peptide fingerprinting software, such as provided by peptide mass fingerprint software, available from matrixsciences.com or prospector.ucsf.edu.

The foregoing disclosure of the preferred embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A system comprising:
   a liquid chromatograph into which a sample is injected to separate entities in the sample, and to determine a retention time associated with each of the one or more entities;
   a mass spectrometer into which the entities are input to determine a mass of each of the one or more entities; and
   a computer programmed to perform processing and computer code, that when executed, causes the computer to perform said processing comprising:
      choosing a subset of entities from a first injection;
      choosing a subset of entities from a second injection;
      comparing the entities chosen from the first injection to those chosen from the second injection;
      identifying entities chosen from the first injection that match entities chosen from the second injection, wherein a first entity having a first mass and a first retention time in the first injection is considered a match for a second entity having a second mass and a second retention time in the second injection in accordance with criteria including determining a match between the first entity and the second entity if a magnitude of difference between the first mass and second mass is below a mass threshold, if a magnitude of difference between the first retention time and the second retention time is below a coarse retention time threshold and if the second entity is the only such entity in the second injection meeting the mass threshold and the coarse retention time threshold with respect to said first entity;
      constructing a retention time map based on the matching entities of the subsets determined by said identifying, said constructing including determining a delta retention time value and a filtered retention time drift for each pair of matching entities including a first entity from the first injection and a second entity from the second injection;
      assigning, based on the retention time map, reference retention times to all entities in the first injection and the second injection, wherein reference retention times are assigned to entities in the second injection using the filtered retention time drifts determined in said constructing;
      determining a set of differences, said set of differences including, for each pair of matching entities, a difference between the delta retention time value for said each pair and said filtered retention time drift for said each pair;
      determining a fine retention time threshold based on the set of differences; and
      tracking, in accordance with tracking criteria including the mass threshold and the fine retention time threshold that is less than the coarse retention time threshold, entities through the first and second injections using the reference retention times and mass values.

2. The system recited in claim 1, said processing further comprising:
   sorting the matched entities.

3. The system recited in claim 1, said processing further comprising:
   determining whether an entity has a corresponding entry in the retention time map;

using a defined value of retention time if the entity has a corresponding entry in a look-up table;

using an interpolated value of retention time if the entity does not have a corresponding entry in the look-up table.

4. The system of claim 1, wherein the first injection is a reference injection and a reference retention time assigned to each entity in the first injection is said each entity's retention time from the first injection.

5. The system of claim 1, wherein the subset of entities chosen from the first injection have intensities higher than a predetermined threshold.

6. The system of claim 1, wherein the subset of entities chosen from the second injection have intensities higher than a predetermined threshold.

7. The system of claim 1, wherein each pair of matching entities satisfies intensity ratio matching requirements such that the intensity ratio of the first entity with respect to the second matching entity is more than a first value and also less than a second value.

8. The system of claim 1, wherein the retention time map includes pairs of values, each of said pairs including a first value that is a retention time of one entity in said second injection determined by said identifying to have a matching entity in said first injection, and a second value that is a reference retention time assigned to the one entity thereby indicating a retention time for the one entity if said one entity were in the first injection rather than the second injection.

9. The system of claim 1, wherein said tracking uses said tracking criteria and identifies one entity in the first injection that matches another entity in the second injection whereby the one entity and the another entity are determined to be a same entity.

10. The system of claim 1, said processing further comprising:

filtering the delta retention time value for each pair of matching entities to determine the filtered retention time drift for each pair of matching entities.

11. The system of claim 10, wherein the filtering is median filtering.

12. A system for tracking entities in an LC/MS system, comprising:

a liquid chromatograph into which the sample is injected to separate entities in the sample, and to determine a retention time associated with each of the one or more entities;

a mass spectrometer into which the entities are input to determine a mass of each of the one or more entities; and a computer programmed for:

choosing, based on intensity, a subset of entities from a first injection and a subset of entities from a second injection;

comparing the entities chosen from the first and second injections;

identifying matching entities chosen from the first and second injections, wherein a first entity having a first mass and a first retention time in the first injection is considered a match for a second entity having a second mass and a second retention time in the second injection in accordance with criteria including determining a match between the first entity and the second entity if a magnitude of difference between the first mass and second mass is below a mass threshold, if a magnitude of difference between the first retention time and the second retention time is below a coarse retention time threshold and if the second entity is the only such entity in the second injection meeting the mass threshold and the coarse retention time threshold with respect to said first entity;

constructing a retention time map based on the matching entities determined by said identifying, said constructing including determining a delta retention time value and a filtered retention time drift for each pair of matching entities including a first entity from the first injection and a second entity from the second injection;

assigning reference retention times to all entities in the first injection and the second injection based on the retention time map, wherein reference retention times are assigned to entities in the second injection using the filtered retention time drifts determined in said constructing;

determining a set of differences, said set of differences including, for each pair of matching entities, a difference between the delta retention time value for said each pair and said filtered retention time drift for said each pair;

determining a fine retention time threshold based on the set of differences; and tracking, in accordance with tracking criteria including the mass threshold and the fine retention time threshold that is less than the coarse retention time threshold, entities through the first and second injections using the retention time map and mass values.

13. The system recited in claim 12, wherein the computer is further programmed to sort the matching entities.

14. The system recited in claim 12, wherein the computer is further programmed for:

determining whether an entity has a corresponding entry in the retention time map;

using a defined value of retention time if the entity has a corresponding entry in a look-up table; and using an interpolated value of retention time if the entity does not have a corresponding entry in the look-up table.

* * * * *